(12) United States Patent
Ebenbeck et al.

(10) Patent No.: US 7,045,662 B2
(45) Date of Patent: May 16, 2006

(54) α,α-DIFLUOROAMINES AND DIFLUOROMETHYLENE-α,α-DIAZO COMPOUNDS

(75) Inventors: Wolfgang Ebenbeck, Leverkusen (DE); Albrecht Marhold, Leverkusen (DE); Alexander Kolomeitsev, Bremen (DE); Gerd-Volker Röschenthaler, Bremen (DE)

(73) Assignee: Bayer Chemicals AG, Levekusen (DE)

( * ) Notice: Subject to any disclaimer, the term of this patent is extended or adjusted under 35 U.S.C. 154(b) by 0 days.

(21) Appl. No.: 10/751,824

(22) Filed: Jan. 5, 2004

(65) Prior Publication Data

US 2004/0198975 A1     Oct. 7, 2004

(30) Foreign Application Priority Data

Jan. 7, 2003    (DE) ............... 103 00 113

(51) Int. Cl.
  *C07C 209/78*    (2006.01)
(52) U.S. Cl. .................... 564/496; 564/248
(58) Field of Classification Search ............... 564/248, 564/496

See application file for complete search history.

(56) References Cited

U.S. PATENT DOCUMENTS

| | | | |
|---|---|---|---|
| 3,092,637 A | 6/1963 | Brown | 260/326.5 |
| 6,242,654 B1 | 6/2001 | Goto et al. | 568/655 |
| 6,329,529 B1 | 12/2001 | Sonoda et al. | 548/300.1 |
| 6,458,990 B1 | 10/2002 | Sonoda et al. | 560/219 |
| 6,632,949 B1 | 10/2003 | Sonoda et al. | 548/300.1 |
| 2002/0042521 A1 | 4/2002 | Sonoda et al. | 548/300.1 |
| 2003/0004348 A1 | 1/2003 | Sonoda et al. | 544/334 |
| 2004/0073065 A1 | 4/2004 | Hidaka et al. | 564/384 |

FOREIGN PATENT DOCUMENTS

JP    60 243 039    12/1985

OTHER PUBLICATIONS

Ziman, S.D., Synthesis fo Cyclic and Acyclic Tri- and Tetrasubstitued Hydroxyguanidines. Journal of Organic Chemistry (1976), vol. 41, No. 20, pp. 3253-3255.*
Database CASREACT on STN, AN: 95:42254, Allenstein et al., Zeitschrift fuer Anorganische und Allgemeine Chemie (1981), 474, p. 7-17 (abstract).*
J. Fluorine Chem., 23, (month unavailable), 1983, p. 219-228, W. Dmowski et al, "Dialkyl-α,α-Difluorobenzylamines and Dialkyl(Trifluoromethyl)Amines—Novel Fluorinating Reagents".
Z. anorg. Allg. Chem., 537 (month unavailable) 1986, p. 63-78, D. J. Brauer et al, "Darstellung, Schwingungsspektren und Kristallstrukturanalyse von Di- und Trifluor-tetramethylammonium-Salzen" (XP008028797).
J. Amer. Chem. Soc., Bd. 84, Nr. 22, (Month unavailable), 1962, p. 4275-4285, F. S. Fawcett et al, "The Chemistry of Carbonyl Fluoride. I. The Fluorination of Organic Compounds", (XP002274553), US American Chemical Society, Washington, DC, Seite 4281-2, Spalte E.
Chemical Physice Letters, Bd. 239, Nr. 4, (month unavailable) 1995, Seiten 320-325, (XP0001189055), NLNorth-Holland, Amsterdam.
Bulletin of Academy of Sciences of the USSR, Div. of Chem. Sci., Bd 30, Nr. 4, Oct. 10, 1981, Seiten 639-642, I. L. Knunyants et al, "Alpha-fluoroalkylamines, a new source of unhydrated fluoride ion", (XP002274542), US Consultants Bureau, NY.

* cited by examiner

Primary Examiner—Brian Davis
(74) Attorney, Agent, or Firm—Jennifer R. Seng

(57) ABSTRACT

The present invention relates to a process for preparing α,α-difluoroamines, difluoromethylene-α,α-diazo compounds and fluorination reagents containing α,α-difluoroamines and/or difluoromethylene-α,α-diazo compounds.

13 Claims, No Drawings

α,α-DIFLUOROAMINES AND DIFLUOROMETHYLENE-α,α-DIAZO COMPOUNDS

BACKGROUND OF THE INVENTION

1. Field of the Invention

The present invention relates to a process for preparing α,α-difluoroamines, difluoromethylene-α,α-diazo compounds and fluorination reagents containing α,α-difluoroamines and/or difluoromethylene-α,α-diazo compounds.

2. Brief Description of the Prior Art

α,α-difluoroamines and difluoromethylene-α,α-diazo compounds have proved to be particularly suitable as reagents for fluorinating alcohols or carbonyl compounds, such as ketones, carboxylic acids and aldehydes. Illustrative thereof is N,N-dimethyl-1,1-difluorobenzylamine which has been used for the fluorination of secondary alcohols and carboxylic acids. However, this method of fluorination is disadvantaged in that it requires, the use of the toxic sulphur tetrafluoride (*J. Fluorine Chem.* 1983, 23, 219–228).

EP-A 895 991 and EP-A 1 013 629 disclose difluoromethylene-α,α-diazo compounds, in particular 2,2-difluoro-1,3-dimethylimidazolidine, which can be used for fluorinating hydroxyl and carboxyl functions. The preparation is customarily carried out in a two-stage reaction, wherein corresponding urea derivatives are first reacted with a chlorinating agent, and then with ionic fluoride to give the desired products. However, the only moderate yields are obtained here. Illustratively, the chlorine-fluorine exchange only proceeds with a yield of 77% of theory (EP-A 1013 629, p. 145 Example 1).

There is, therefore, a need to provide a process for preparing α,α-difluoroamines and difluoromethylene-α,α-diazo compounds which can be carried out without special safety measures and in high yields.

SUMMARY OF THE INVENTION

A process has now been found for preparing compounds of the formula (I),

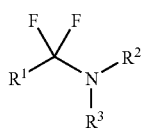
(I)

where $R^1$ represents hydrogen, $C_1$–$C_{12}$-alkyl, [($C_2$–$C_{12}$-alkylene)-O]$_n$($C_1$–$C_{12}$-alkyl)] where n=1 to 5, $C_3$–$C_{14}$-aryl, $C_4$–$C_{15}$-arylalkyl or $NR^4R^5$, where $R^4$ and $R^5$ each independently of one another represent $C_1$–$C_8$-alkyl or $NR^4R^5$ as a whole represents a 4 to 7-membered cyclic radical having a total of 3 to 16 carbon atoms and $R^2$ and $R^3$ each independently of one another represent $C_1$–$C_{12}$-alkyl, $C_3$–$C_{14}$-aryl or $C_4$–$C_{15}$-arylalkyl, or together are part of a cyclic radical having a total of 3 to 16 carbon atoms, or $R^1$ and $R^2$ and/or $R^3$ are together part of a cyclic radical having a total of 3 to 16 carbon atoms, which is characterized in that compounds of the formula (II)

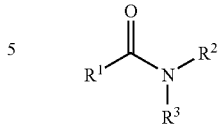
(II)

where $R^1$, $R^2$ and $R^3$ have the meanings given above are reacted in the presence of oxalyl fluoride and/or difluorophosgene, with or without organic solvent.

In the context of the invention, all radical definitions and parameters mentioned generally or in preferred ranges can be combined with one another, that is to say also combined in a desired manner between the respective ranges and preferred ranges.

It may be noted that the depiction of formula (I) chosen for reasons of simplicity, and frequently used in the literature, also comprises the depiction below, which is to be taken as the most probable structure from our own NMR-spectroscopy studies

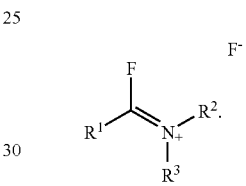

The same applies, in the context of the invention, by analogy to all other depictions and nomenclatures of α,α-dihaloamine functionalities.

DETAILED DESCRIPTION OF THE INVENTION

Alkyl, or alkylene or alkoxy each independently represent a straight-chain, cyclic or branched or unbranched alkyl or alkylene, or alkoxy radical, respectively. The same applies to the non-aromatic part of an arylalkyl radical.

$C_1$–$C_4$-alkyl represents, for example, methyl, ethyl, n-propyl, isopropyl, n-butyl, sec-butyl and tert-butyl, $C_1$–$C_8$-alkyl, furthermore, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, 1-Ethyl-2-methylpropyl, n-heptyl and n-octyl, $C_1$–$C_{12}$-alkyl, furthermore, represents, for example, adamantyl, the isomeric menthyls, n-nonyl, n-decyl and n-dodecyl.

$C_1$–$C_4$-alkoxy represents, for example, methoxy, ethoxy, n-propoxy, isopropoxy, n-butoxy, sec-butoxy and tert-butoxy, $C_1$–$C_8$-alkoxy, furthermore, represents n-pentoxy, 1-methylbutoxy, 2-methylbutoxy, 3-methylbutoxy, neopentoxy, 1 ethylpropoxy, cyclohexoxy, cyclopentoxy, n-hexoxy and n-octoxy, $C_1$–$C_{12}$-alkoxy, furthermore, represents for example, adamantoxy, the isomeric menthoxy radicals, n-decoxy and n-dodecoxy.

$C_2-C_{12}$-alkylene represents, for example, 1,2-ethylene, 1,3-propylene, 1,4-butylene, 1,2-cyclohexoxylene and 1,2-cyclopentylene.

Aryl each independently represents a heteroaromatic radical in which none, one, two or three of the skeleton atoms per cycle, but at least one skeleton atom in the entire molecule, is selected from the group consisting of nitrogen, sulphur and oxygen, or represents a carbocyclic aromatic radical.

Examples of heteroaromatic radicals are pyridinyl, oxazolyl, benzofuranyl, dibenzofuranyl or quinolinyl, examples of carbocyclic aromatic radicals are phenyl, naphthyl, phenanthrenyl, anthracenyl or fluorenyl.

Furthermore, the heteroaromatic or carbocyclic aromatic radical can be substituted with up to five identical or different substituents per cycle which are each independently selected from the group consisting of chlorine, fluorine, $C_1-C_{12}$-alkyl, $C_1-C_{12}$-fluoroalkyl, $C_1-C_{12}$-fluoroalkoxy, $C_1-C_{12}$-fluoroalkylthio, $C_1-C_{12}$-alkoxy, di($C_1-C_8$-alkyl)amino and tri($C_1-C_8$-alkyl)siloxyl.

Arylalkyl each independently represents, a straight-chain, cyclic branched or unbranched alkyl radical according to the definition above which is monosubstituted, polysubstituted, or completely substituted by aryl radicals according to the definition above.

The preferred substitution patterns are defined below for compounds of the formula (I):
$R^1$ preferably represents hydrogen, $C_1-C_{12}$-alkyl, or $C_3-C_6$-aryl, particularly preferably hydrogen or $C_1-C_8$-alkyl, and very particularly preferably hydrogen or $C_1-C_4$-alkyl.
$R^2$ and $R^3$ each independently of one another preferably represent $C_1-C_8$-alkyl or $NR^2R^3$ as a whole represents N-morpholinyl, N-methyl-1,4-piperazin-N-yl, and particularly preferably in each case identically represent methyl, ethyl or isopropyl.

Likewise, preferably, formula (I) as a whole represents 2,2-difluoroimidazoline, 2,2-difluoropyrrolidine or 2,2-difluoropiperidinyl, [2,2,2]-2,2,5,5-tetrafluoro-1,4-diazabicyclooctane or [2,2,2]-2,2,6,6-tetrafluoro-1,4-diazabicyclooctane, in which case the said radicals can if appropriate be monosubstituted or polysubstituted by $C_1-C_4$-alkyl.

Compounds of the formula (I) which may be mentioned are:
1,1-difluoromethyl-N,N-dimethylamine, 1,1-difluoromethyl-N,N-diethylamine, 1,1-difluoromethyl-N,N-diisopropylamine, 1,1-difluoro-N,N-2-trimethyl-1-propanamine, 1,1-difluoro-N,N-2,2-tetramethyl-1-propanamine, N,N-diethyl-α,α-difluoro-2,2-dimethyl-1-propanamine, N-(1,1-difluoromethyl)morpholine, 1,1-difluoro-N,N-dimethylphenylmethanamine, N,N-diethyl-α,α-difluoro-3-pyridylmethanamine, N,N-diethyl-α,α-difluoro-2-pyridylmethanamine, diethyl-α,α-difluoro-(4-chlorophenyl)methanamine, N,N-diisopropyl-α,α-difluorophenylmethanamine, N,N-diethylyl-α,α-difluorophenylmethanamine, N,N-dimethylα,α-difluorophenylmethanamine, 2,2-difluoro-1,3-dimethylimidazolidine and 2,2-difluoro-1,3,3-trimethylpyrrolidine, [2,2,2]-2,2,5,5-tetrafluoro-3,3,6,6-tetramethyl-1,4-diazabicyclooctane and [2,2,2]-2,2,6,6-tetrafluoro-3,3,5,5-tetramethyl-1,4-diazabicyclooctane.

Compounds of the formula (I) are preferably reacted in the presence of organic solvent.

Suitable organic solvents are, for example, aliphatic, alicyclic or aromatic, if appropriate halogenated, hydrocarbons, for example various benzynes, benzene, toluene, xylene, chlorobenzene, dichlorobenzene, various petroleum ethers, hexane, cyclohexane, dichloromethane, chloroform, carbon tetrachloride; ethers, such as diethyl ether, methyl tert-butyl ether, diisopropyl ether, dioxane, tetrahydrofuran or ethylene glycol dimethyl ether or ethylene glycol diethyl ether; nitriles, such as acetonitrile, propionitrile, benzonitrile, benzyl nitrile or butyronitrile; sulphones such as tetramethylene sulphone; benzotrifluoride, or mixtures of such organic solvents.

Preferably, the water content of the solvent in the inventive process is at most 0.2% by weight, preferably at most 0.05% by weight. Preferably, such a water content is achieved by distilling or drying in a manner known per se.

The molar ratio of oxalyl fluoride and/or difluorophosgene to compounds of the formula (II) is, for example, and preferably, 0.8:1 to 20:1, preferably 1:1 to 2:1, and particularly preferably 1.02:1 to 1.1:1. It is possible to use larger amounts, but this does not improve the yields.

The reaction temperature can be, for example, −50° C. to 100° C., preferably −10° C. to 50° C.

The reaction pressure can be, for example, 0.8 to 20 bar, preferably 1.5 to 5 bar.

After the reaction, the product can be worked up, for example, by distilling off all volatile constituents and drying the residue in a high vacuum.

In the manner according to the invention, the compounds of the formula (I) are obtained in high yield and purity.

Surprisingly, it has been found that compounds of the formula (1) function more efficiently as fluorination reagent if they are used in the presence of a tertiary aprotic amine and/or a N-heteroaromatic compound, and in the presence of hydrogen fluoride. Therefore, the invention in a presently preferred embodiment also comprises a process which comprises, as further step, reacting the inventively prepared compounds of the formula (I) with at least one, preferably precisely one, aprotic tertiary amine which does not contain fluorine atoms in the α position to the nitrogen and/or at least one, preferably precisely one, N-heteroaromatic compound and hydrogen fluoride.

Aprotic, in this context, means that the tertiary amine, which can also be a molecule having a plurality of tertiary amino groups, does not bear any hydrogen atoms which have a pKa of less than 20, based on an aqueous reference scale at 25° C.

It may be noted that under the definitions chosen above for reasons of simplicity, the corresponding tertiary ammonium fluorides, N-heteroarylium fluorides, and the corresponding polyfluorides and also the polyfluorides of ionic compounds are also comprised by the formula (I) (see Figure (Ia)), which occur in the reaction of tertiary amines and/or N-heteroaromatic compounds or compounds of the formula (I) and hydrogen fluoride.

Preferred aprotic tertiary amines are those of the formula (IIIa) and (IIIb)

$NR^6R^7R^8$ (IIIa)

$(R^9)N-F-N(R^9)_2$ (IIIb)

where
$R^6$, $R^7$ and $R^8$ each independently of one another represent $C_1-C_{12}$-alkyl or $[(C_2-C_{12}\text{-alkylene})-O]_n(C_1-C_{12}\text{-alkyl})]$ where n=1 to 5, or two or three of the radicals $R^6$, $R^7$ and/or $R^8$ together with the nitrogen atom form a monocyclic or bicyclic radical having a total of 3 to 16 or 5 to 20 carbon atoms respectively and $R^9$ each independently represents $C_1$–$C_{12}$-alkyl or in each case two of the four radicals together represent a $C_2$–$C_8$-alkylene radical and F represents $C_2$–$C_8$-alkylene.

In formula (IIIa) $R^6$, $R^7$ and $R^8$ each independently of one another preferably represent $C_1$–$C_{12}$-alkyl, in the formula particularly preferred, each identically represents $C_1$–$C_8$-alkyl. Particularly preferred aprotic tertiary amines of the formulae (IIIa) and (IIIb) are triethylamine, diazabicyclooctane and tetramethylethylenediamine.

Preferred N-heteroaromatic compounds are unsubstituted or substituted pyridines and quinolines, pyridine being particularly preferred.

The molar ratio of aprotic tertiary amine to compounds of the formula (I) is, for example and preferably, 0.1:1 to 20:1, preferably 1:1 to 10:1.

The molar ratio of hydrogen fluoride to aprotic tertiary amine and/or N-heteroaromatic compounds is, for example and preferably, 0.2:1 to 10:1 per nitrogen atom.

For the reaction with aprotic tertiary amine and/or N-heteroaromatic compounds and hydrogen fluoride, a procedure can be followed, for example, such that compounds of the formula (I) are charged and are reacted first with aprotic tertiary amine and/or N-heteroaromatic compounds and then with hydrogen fluoride, or first with hydrogen fluoride and then with aprotic tertiary amine or N-heteroaromatic compounds, or are preferably reacted with mixtures of aprotic tertiary amine or N-heteroaromatic compounds and hydrogen fluoride which are also commercially available in various compositions, for example (NEt$_3$×3HF) or (pyridine× 9HF). Other orders of addition also lead to success in the same manner.

The inventively preferable compounds of the formula (I) or mixtures thereof with tertiary aprotic amine and/or N-heteroaromatic compounds and hydrogen fluoride are suitable, in particular, for preparing fluorine compounds from the corresponding hydroxyl compounds, and also for preparing geminal difluoro compounds from the corresponding carbonyl compounds. Preferred fluorine compounds are those which are used for preparing agrochemicals, drugs and liquid crystals.

The inventive process has the advantage that the compounds of the formula (I) or mixtures thereof with tertiary aprotic amine and/or N-heteroaromatic compounds and hydrogen fluoride start from readily available starting materials and supply the desired products with very simple workup at very high purities and yields.

EXAMPLES

Example 1

Preparation of 1,1-difluoro-N,N-2,2-tetramethyl-1-propanamine

Under a protective gas atmosphere, 2.58 g (20 mmol) of N,N-dimethylpivalamide are charged together with 10 ml of CH$_2$Cl$_2$ in a steel cylinder. The batch is cooled down to –10° C. and to this are added 2 g (21.3 mmol) of precooled oxalyl fluoride. The reaction vessel is sealed, the batch is allowed to come up to room temperature and is then heated with stirring for a further 16 h to 40° C. After the reaction is complete (GC), it is allowed to cool back to 20° C. After the solvent has been taken off in a water-jet vacuum, 1,1-difluoro-N,N-2,2-tetramethyl-1-propanamine is obtained as a light yellow liquid.

Yield: 2.85 g (18.5 mmol; 93%; purity: 99% (based on area)

$^1$H-NMR (CDCl$_3$): 1.00 (broad s, 9H, t-Bu-H), 2.26 (t, 6H, $^4$JHF=1.95 Hz, N(CH$_3$)$_2$) ppm.

$^{13}$C-NMR (C$_6$D$_6$): 25.7 (s, CH$_3$, 3C, t-Bu-CH$_3$), 38.3 (t, CH$_3$, $^3$JCF=6.03 Hz, N(CH$_3$)$_2$), 40.0 (t, quart. C, 1C, $^2$J$_{CF}$=29.8 Hz, t-Bu-C), 128.6 (t, CF$_2$, 1C, $^1$J$_{CF}$=258.1 Hz) ppm.

$^{19}$F-NMR (CDCl$_3$): –97.5 (s, —CF$_2$) ppm.

Example 2

Preparation of a Fluorination Reagent Containing 1,1-difluoromethyl-N,N-diisopropylamine Under a protective gas atmosphere, 10.4 g (69 mmol) of 1,1-difluoromethyl-N,N-diisopropylamine, which was prepared in a similar manner to Example 1 in a yield of 92% of theory, was charged in a polyethylene flask and cooled to 0° C. To this are added 11.1 g (69 mmol) of NEt$_3$.3HF in the course of 2 min and the mixture is stirred for a further 20 min at this temperature. The initially liquid-crystalline reaction mixture is allowed to come to 20° C., is heated for homogenization to 40° C. for 0.5 h and is allowed to cool back to 20° C. 21.5 g (69 mmol) of i-Prop$_2$N=CHF$^+$HF$_2^-$.HNEt$_3^+$. HF$_2^-$ results therefrom having a melting point of 37–40° C.

$^{19}$F-NMR (CD$_2$Cl$_2$): –86.7 (br s, 1F, CHF$^+$), –158.5 (br s, 4F, HF$_2^-$) ppm.

Example 3

Reacting 1-phenylethanol with the Fluorination Reagent from Example 2

Under a protective gas atmosphere 0.83 g (6.8 mmol) of 1-phenylethanol is added dropwise in the course of 5 min to a solution of 2.32 g (7.56 mmol) of i-Prop$_2$N=CHF$^+$HF$_2^-$ .HNEt$_3^+$.HF$_2^-$ in 10 ml of CH$_2$Cl$_2$ in a polyethylene container. The mixture is stirred for several hours at 20° C. and the conversion rate is analysed by $^{19}$F-NMR (reference: PhCF$_3$). After 2.5 h, 81% of 1-fluoroethylbenzene is obtained, and after a stirring time of 24 h, 96% of product is obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing at least one compound of the formula (I)

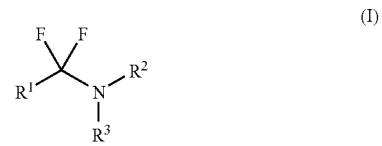

(I)

wherein $R^1$ represents hydrogen, $C_1$–$C_{12}$-alkyl, [($C_2$–$C_{12}$-alkylene)-O]$_n$($C_1$–$C_{12}$-alkyl)] where n=1 to 5, $C_3$–$C_{14}$-aryl, $C_4$–$C_{15}$-arylalkyl or NR$^4$R$^5$, where $R^4$ and $R^5$ each independently of one another represent $C_1$–$C_8$-alkyl or NR$^4$R$^5$ as a whole represents a 4 to 7-membered cyclic radical having a total of 3 to 16 carbon atoms and R² and R³ each independently of one another represent C₁–C₁₂-alkyl, C₃–C₁₄-aryl or C₄–C₁₅-arylalkyl, or together are part of a cyclic radical having a total of 3 to 16 carbon atoms, or R¹ and R² and/or R³ are a cyclic radical having a total of 3 to 16 carbon atoms; comprising reacting compounds of the formula (II)

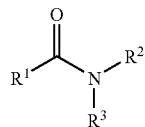
(II)

wherein
R¹, R² and R³ have the meanings given above in the presence of oxalyl fluoride or a mixture of oxalyl fluoride and difluorophosgene.

2. A process according to claim 1, characterized in that the reaction takes place in the presence of organic solvent.

3. A process according to claim 1, characterized in that R¹ represents hydrogen, C₁–C₁₂-alkyl or C₃–C₆-aryl.

4. A process according to claim 1, characterized in that the radicals R² and R³ each independently of one another represent C₁–C₈-alkyl, or NR²R³, which as a whole, represents N-morpholinyl, N-methyl-1,4-piperazin-N-yl, or R¹CF₂R², which as a whole, represents 2,2-difluomimidazolinyl, 2,2-difluoropyrrolidinyl, 2,2-difluoropiperidinyl or [2,2,2]-2,2,5,5-tetrafluoro-1,4-diazabicyclooctane or [2,2,2]-2,2,6,6-tetrafluoro-1,4-diazbicyclo-octane, in which case the radicals are optionally monosubstituted or disubstituted by C₁–C₄-alkyl.

5. A process according to claim 1, characterized in that the compounds of the formula (I) prepared are: 1,1-difluoromethyl-N,N-dimethylamine, 1,1-difluoromethyl-N,N-diethylamine, 1,1-difluoromethyl-N,N-diisopropyl-amine, 1,1-difluoro-N,N-2-trimethyl-1-propanamine, 1,1-difluoro-N,N,2,2-tetramethyl-1-propanamine, N,N-diethyl-α,α-difluoro-2,2-dimethyl-1-propanamine, N-(1,1-difluoromethyl)morpholine, 1,1-difluoro-N,N-dimethylphenylmethanamine, N,N-diethyl-α,α-difluoro-3-pyridylmethanamine, N,N-diethyl-α,α-difluoro-2-pyridylmethanamine, diethyl-α,α-difluoro-(4-chlorophenyl)methanamine N,N-diisopropyl-α,α-difluorophenylmethanamine, N,N-diethylyl-α,α-difluorophenylmethanamine, N,N-dimethyl-α,α-difluorophenylmethanamine, 2,2-difluoro-1,3-dimethylimidazolidin, 2,2-difluoro-1,3,3-trimethylpyrrolidine, [2,2,2]-2,2,5,5-tetrafluoro-3,3,6,6-tetramethyl-1,4-diazabicyclooctane and [2,2,2]-2,2,6,6-tetrafluoro-3,3,5,5-tetramethyl-1,4-diazabicyclooctane.

6. A process according to claim 1, characterized in that the molar ratio of oxalyl fluoride to compounds of the formula (II) is 0.8:1 to 20:1.

7. A process according to claim 1, characterized in that the reaction temperature is from −50° C. to 100° C.

8. A process according to claim 1, characterized in that the reaction pressure is from 0.8 to 20 bar.

9. A process according to claim 1, wherein the process further comprises reacting the resulting compounds of formula (I) with
at least one aprotic, tertiary amine which does not contain fluorine atoms in the α position to the nitrogen and/or
at least one N-heteroaromatic compound and
hydrogen fluoride.

10. A process according to claim 9, characterized in that the molar ratio of aprotic tertiary amine and/or N-heteroaromatic compounds to compounds of the formula (I) is 0.1:1 to 20:1 and the molar ratio of hydrogen fluoride to aprotic tertiary amine is 0.2:1 to 10:1.

11. A process for preparing fluorine compounds from corresponding hydroxyl compounds comprising reacting the hydroxyl compounds with compounds which have been prepared according to claim 9.

12. A process for preparing for preparing geminal difluorocompounds from the corresponding carbonyl compounds comprising reacting the carbonyl compounds with compounds which have been prepared according to claim 9.

13. A fluorinating reagent prepared according to the process of claim 9.

* * * * *